(12) United States Patent
A. et al.

(10) Patent No.: US 11,752,032 B2
(45) Date of Patent: *Sep. 12, 2023

(54) FLUIDIC BLADDER PRESSURE CONTROL IN A THERAPEUTIC SYSTEM

(71) Applicant: VASPER SYSTEMS, LLC, Kamuela, HI (US)

(72) Inventors: Chesavage Jay A., Palo Alto, CA (US); Marshall Lise, Mountain View, CA (US); Gregory A. Chesavage, San Jose, CA (US)

(73) Assignee: Vasper Systems, LLC, Kamuela, HI (US)

( * ) Notice: Subject to any disclaimer, the term of this patent is extended or adjusted under 35 U.S.C. 154(b) by 396 days.

This patent is subject to a terminal disclaimer.

(21) Appl. No.: 17/027,686

(22) Filed: Sep. 21, 2020

(65) Prior Publication Data

US 2021/0015660 A1    Jan. 21, 2021

Related U.S. Application Data

(63) Continuation of application No. 14/957,556, filed on Dec. 2, 2015, now Pat. No. 10,806,625.

(Continued)

(51) Int. Cl.
  *A61F 7/02* (2006.01)
  *A61F 7/00* (2006.01)

(52) U.S. Cl.
  CPC ........ *A61F 7/02* (2013.01); *A61F 2007/0029* (2013.01); *A61F 2007/0039* (2013.01);
  (Continued)

(58) Field of Classification Search
  CPC ...... A61H 9/00; A61H 9/0078; A61H 9/0085; A61H 9/0092; A61H 2201/02; A61H 2201/0103; A61H 2201/0214; A61H 2201/0242; A61H 2201/5056; A61F 7/00; A61F 7/02; A61F 2007/0029; A61F 2007/0039; A61F 2007/0056; A61F 2007/0091; A61F 2007/0092; G01L 7/00–24; G01L 9/00–18;
  (Continued)

(56) References Cited

U.S. PATENT DOCUMENTS 4,735,727 A * 4/1988 Heitmeier ............... A61M 1/16
                                                   210/321.71
6,176,869 B1 * 1/2001 Mason ...................... A61F 7/02
                                                         607/104

(Continued)

*Primary Examiner* — Rachel T Sippel
*Assistant Examiner* — Jacqueline M Pinderski
(74) *Attorney, Agent, or Firm* — File-EE-Patents.com; Jay A. Chesavage

(57) ABSTRACT

A process for a therapeutic bladder pressure estimator is operative with a pump connected, in sequence, to a first hose, a supply pressure sensor, a second hose, a bladder having an inlet coupled to the second hose, a bladder outlet coupled to a third hose of substantially equal length to the second hose, a return pressure sensor, and a fourth hose coupled to the return pressure sensor and returning fluid from the pump to the reservoir. The process forms an error signal from the difference between a setpoint and the average of the supply and return pressures. A head pressure measurement may be done by turning the pump off after a steady state reading is made.

19 Claims, 5 Drawing Sheets

Related U.S. Application Data

(60) Provisional application No. 62/088,529, filed on Dec. 5, 2014.

(52) U.S. Cl.
CPC ............... *A61F 2007/0056* (2013.01); *A61F 2007/0092* (2013.01)

(58) Field of Classification Search
CPC ......... G01L 11/00–06; G01L 13/00–06; G01L 15/00; G01L 17/00–005; G01L 19/00–16
See application file for complete search history.

(56) References Cited

U.S. PATENT DOCUMENTS

| | | | | |
|---|---|---|---|---|
| 6,450,981 B1 * | 9/2002 | Shabty | ................ | A61H 31/008 601/150 |
| 10,806,625 B1 * | 10/2020 | Chesavage | ............ | A61F 7/0085 |
| 2012/0065561 A1 * | 3/2012 | Ballas | ................ | A61H 9/0092 601/152 |

* cited by examiner

Pressure Control System

Flow Schematic

Pressure Control System

Four Cuff Arm/Leg Pressure/Cooling System
600

FLUIDIC BLADDER PRESSURE CONTROL IN A THERAPEUTIC SYSTEM

FIELD OF THE INVENTION

The present invention relates to a system and method for measurement or regulation of pressure inside a bladder. In particular, the system relates to the measurement and regulation of pressure in a bladder having an input line and an output line and pressurized to a setpoint using a circulating fluid, and with an elevation difference between a remote measurement point and a bladder having an internal bladder setpoint pressure to measure or regulate.

BACKGROUND OF THE INVENTION

Measurement of fluidic pressure in a fluid-carrying bladder can be readily performed at the bladder using a pressure gauge or pressure sensor. However, when there is a circulating fluid through the bladder and the pressure sensor is remotely located from the bladder, several errors are introduced. A first error is an offset error associated with the fluid density and elevation difference between the bladder and pressure sensor. When the objective of the bladder is compression of a wearable cuff, the fluid used to pressurize the bladder can be air, in which case the added pressure from the elevation difference between bladder and sensor is a negligible 0.0323 Pascals (Pa) per mm. However, when the objective of the bladder is also cooling of an encircled limb, water or other liquid with greater density and greater thermal transfer characteristics may be used. Where water is used as a coolant, the added fluid pressure from the elevation difference between the fluid and pressure sensor measurement point, known as "head pressure", increases to 9.8 Pa per mm of head height. In an example where the bladder pressure is 50 mmHg (6.67 kPa), and the pressure sensor is 750 mm below the bladder, the head pressure from the water in the lines from the bladder to the pressure sensor is 7.3 kPa, in excess of the intrinsic 6.67 kPa pressure to be measured. Further, when it is desired to measure the fluid pressure in the presence of fluid flow, the problem becomes yet more complicated by the pressure drops across the lines from turbulent flow in the fluid supply and return lines.

It is desired to provide a method and apparatus for measurement of fluidic pressure where a fluid is circulating through a bladder with a height difference between the bladder and the pressure sensor.

OBJECTS OF THE INVENTION

A first object of the invention is a measurement system for estimation of the pressure of a fluid circulating through a bladder, the system having, in sequence, a pump coupled to a reservoir, a first fluid line coupled to a supply pressure sensor, a second fluid line coupled to a bladder inlet port, a bladder outlet port coupled to a third fluid line of substantially equal flow parameters, such as equal inner diameter and length as the second fluid line, the outlet of the third fluid line coupled to a return pressure sensor, the return pressure sensor coupled to a fourth fluid line returning circulated fluid to the reservoir, the pressure measured by taking the average of the supply pressure sensor measurement and return pressure sensor measurement.

A second object of the invention is a pressure control system for regulation of a pressure developed in a bladder to a setpoint, the pressure control system having:

a reservoir coupled to a pump, the pump coupled to, in sequence, a supply pressure sensor, a first fluid line coupled to an inlet port of a bladder, the bladder having an outlet port coupled to the inlet port, the bladder outlet port having a second fluid line coupled to a return pressure sensor, the return pressure sensor having an outlet which is either coupled to a reservoir or to a third fluid line coupled to the reservoir;

the pump controlled by a control system which generates an error signal which is coupled to the pump, the error signal being derived from the difference between the setpoint and the average of the supply pressure sensor measurement and the return pressure sensor measurement.

A third object of the invention is a pressure control system for regulation of a pressure developed in a bladder to a setpoint, the pressure control system having:

a reservoir coupled to a pump, the pump coupled to, in sequence, a supply pressure sensor, a first fluid line coupled to an inlet port of a bladder, the bladder having an outlet port coupled to the inlet port, the bladder outlet port having a second fluid line coupled to a return pressure sensor, the return pressure sensor having an outlet which is either coupled to a reservoir or to a third fluid line coupled to the reservoir;

the pump controlled by a control system which generates an error signal which is coupled to the pump, the error signal being the sum of a first term and a second term, where:

the first term is formed from the product of a first constant multiplied by the difference between the setpoint and the average of the supply pressure and return pressure;

and the second term is formed from the product of a second constant multiplied by the integral of the difference between the setpoint and the average of the supply pressure and return pressure over time.

A fourth object of the invention is the estimation and compensation of head pressure in a system having, in sequence, a reservoir coupled to a pump, a first hose, a supply pressure sensor, a second hose, a bladder inlet, a bladder outlet, a third hose, a return pressure sensor, and fourth hose coupled to the reservoir, the pump operated for a duration sufficient to develop a return pressure indicating the system is charged with coolant, the head pressure estimate formed by turning off the pump and measuring a return pressure and a supply pressure, deriving a head pressure measurement from the return pressure measurement and supply pressure measurement, thereafter adding the head pressure estimate to a pressure setpoint which regulates bladder pressure by coupling an error signal to a pump, the error signal derived from the difference between the sum of the setpoint and head pressure estimate and the average of the supply pressure and return pressure.

SUMMARY OF THE INVENTION

The invention is a pressure measurement and control system for a fluidic bladder carrying a circulating fluid coupled from a pump and a reservoir using a length of supply hose and a length of return hose separating the fluidic bladder from a supply pressure sensor and a return pressure sensor located near the reservoir and pump. In one example of the invention, a circulating pump draws a coolant such as chilled water from a reservoir, pressurizes the coolant, and delivers the coolant, in sequence, to a supply pressure sensor, thereafter through an inlet hose to an inlet port of a cuff bladder, the bladder also having an outlet port coupled to an outlet hose of equal length as the inlet hose, the outlet hose thereafter coupled to an outlet pressure sensor and an exhaust hose, the exhaust hose returning the coolant to the reservoir.

In another example of the invention for estimating or regulating pressure of a remote bladder, the previously described system is actuated during a first interval until a return pressure is measured and the supply and return pressure sensors provide steady state readings, after which the pump is turned off, and the supply and return pressures are read when they are substantially equal to each other, from which a head pressure measurement is derived, the head pressure measurement subsequently added to a setpoint pressure with the system regulating pressure until the setpoint pressure plus the head pressure measurement are substantially equal to the average of the supply pressure sensor measurement and the return pressure sensor measurement.

DETAILED DESCRIPTION OF THE INVENTION

Figure 1:
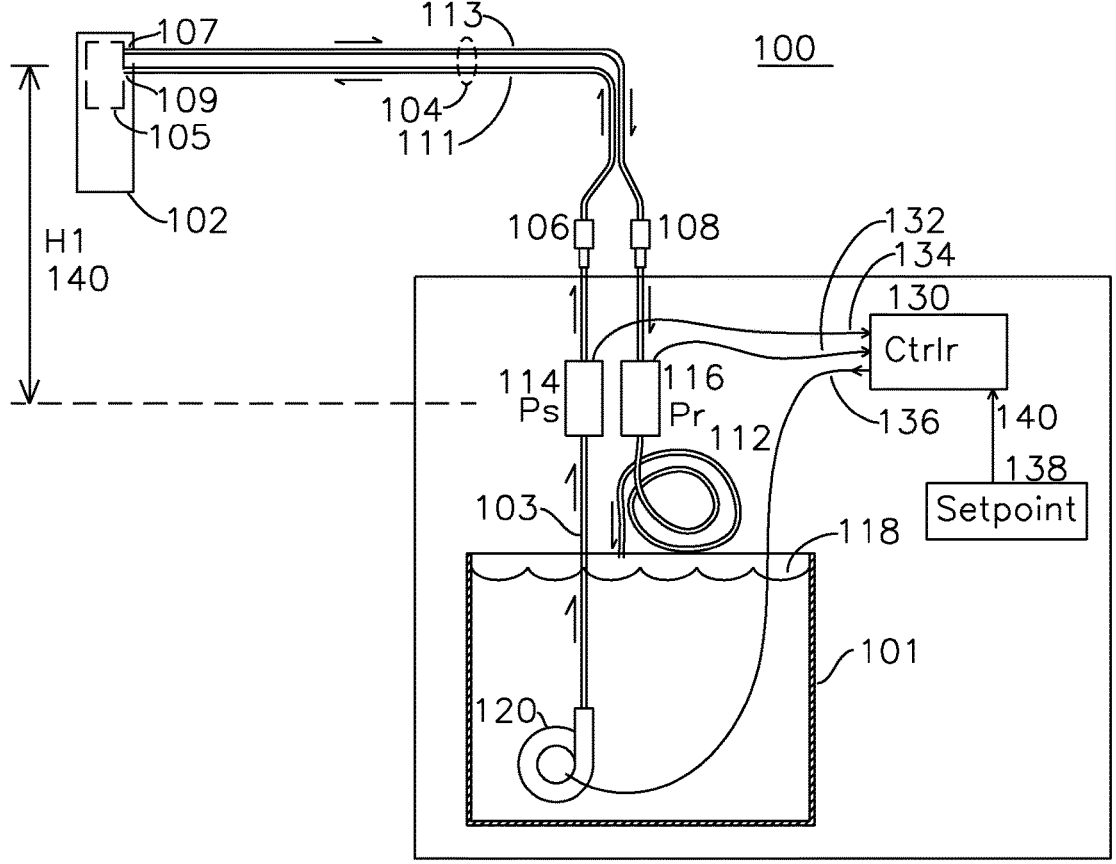
FIG. 1 is a system diagram of a pressure regulation system for a bladder where the bladder is coupled to a reservoir and pressurized through a pump.

FIG. 1 shows an example of a pressure regulation system 100 according to the present invention. Reservoir 101 contains a circulated fluid such as chilled water 118, which is coupled to a pump 120 which may be submerged in and reservoir 101 as shown, or placed externally to the tank and coupled to the fluid via a hose (not shown). Pump outlet hose 103 is coupled to supply pressure sensor 114 which generates an electrical signal 134 indicating measured supply pressure. The supply pressure sensor 114 is coupled through optional removable fluid coupling 106 to a second hose 111 to the inlet port 109 of bladder 105 which is part of pressure cuff 102. Bladder 105 may have a fluid circulation path or enclosed region which is coupled to an outlet port 107 which is coupled to third hose 113, thereafter to optional removable coupler 108, to return pressure sensor 116 which generates an electrical signal 132, and the return pressure sensor 116 is thereafter coupled to fourth hose 112 which returns the circulating fluid to reservoir 101. The pressure controller 130 may be a proportional controller, proportional integral differential (PID) controller, or other digital or analog controller which controls pump 120 speed by varying the power applied to the pump using electrical signal 136. The controller regulates pressure in the cuff 102 bladder 105 by receiving a setpoint pressure 138 as a digital or analog signal 140, and comparing the setpoint pressure 140 to the measured supply pressure 134 and measured return pressure 132, using an algorithm best understood in examination of FIG. 2.

Figure 2:
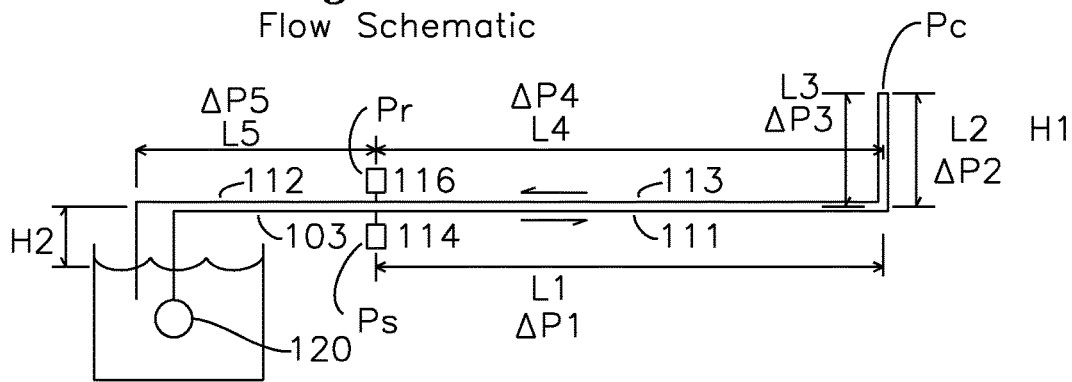
FIG. 2 is a schematic flow diagram of the system of FIG. 1.

FIG. 2 shows a flow schematic of FIG. 1, where the pump 120 pressurizes first line 103 to pressure sensor 114, which measures supply pressure Ps. The bladder is separated from the pressure sensors by a horizontal separation distance L1 plus a vertical separation distance L2, the bladder shown in schematic form as having cuff bladder pressure Pc. The returning fluid travels vertical length L3 and horizontal length L4 and return pressure is measured by return pressure sensor 116. Exhaust liquid travels through a hose of length L5 to reservoir 101. Where the sensors 114 and 116 are at the same elevation above the tank water level H2, and when the supply hose L1 is of equal length as return hose L4, the steady state pressure drop through the hoses 111 and 113 are substantially equal, since in equilibrium the flow velocities are balanced and equal (although the pressures in the hoses decrease along the path length because of turbulent loss). Additionally, the head pressure contributions of L2 and L3 are offsetting, apart from the flow pressure drops of L2 and L3, which are equal for equal flow velocities due to the matched turbulence along 111 and 113. The pressure cuff Pc is a height H1 above the pressure sensors 114 and 116, and the pressure sensors 114 and 116 are a height H2 above the reservoir level.

Figure 4:
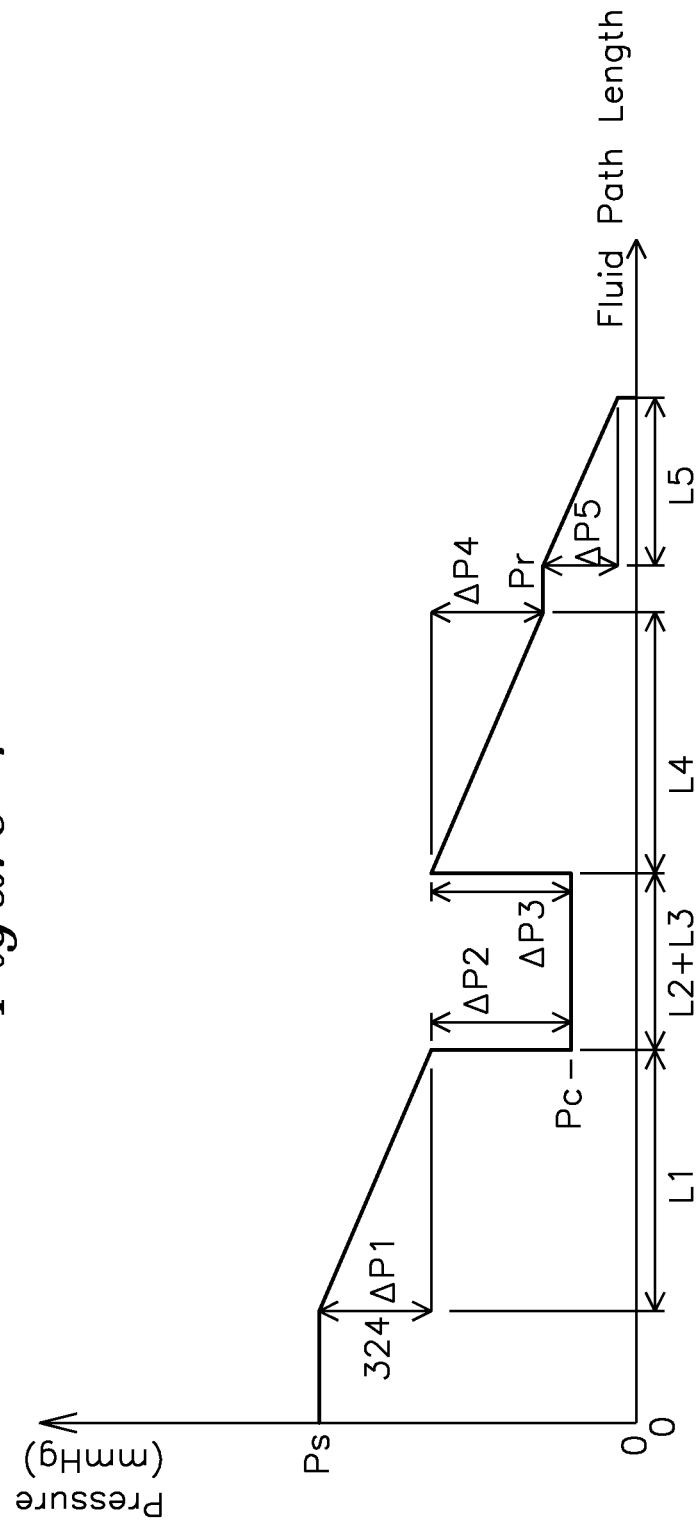
FIG. 4 shows a plot of pressure drops through the fluidic path lengths of FIG. 2.

FIG. 4 shows a plot of the developed pressures along the elements of the system shown schematically in FIG. 2, with the vertical axis indicating the pressure developed at a particular element of the system, and the horizontal axis indicating a particular length of the run. The pressure at the outlet of the pump is shown as Ps, which drops by $\Delta P1$ along the length L1 of the supply tubing, then drops by $\Delta P2$ associated with the vertical change in tubing over L2, where the bladder pressure is Pc. The subsequent vertical drop over L3 regains the pressure $\Delta P3$, which next drops by $\Delta P4$ along L4 to the return pressure indicated as Pr. The final length of tubing L5 drops the pressure to near 0, as it is near the surface of the reservoir at 0 pressure.

Pressure cuff 102 is preferably designed to encircle a human limb with the bladder on the inner surface of the cuff. As the bladder fills, it will apply the pressure of bladder 105 to the encircled limb after bladder 105 has filled to the point that additional volume displacement of the bladder 105 translates into a uniform applied pressure in the encircled limb and bladder 105. The cuff 102 encircles the limb and contains the bladder, thereby ensuring that pressure developed in the bladder is in equilibrium with the pressure transferred to the encircled limb. One example of such a cuff and bladder is described in U.S. Pat. No. 8,273,114, which is incorporated by reference. Another example pressurized cuff, also incorporated by reference, is described in U.S. patent application Ser. No. 13/094,799 filed Apr. 26, 2011 with common assignee as the present application.

The steady state operation of the pressure regulation system of FIGS. 1 and 2 may be derived from the below equations. When the cuff 102 bladder 105 is filled and the bladder 105 reaches equilibrium and a steady-state pressure, the inlet and outlet flow velocities are equal, as was previously indicated. In this steady state mode of operation:

$$Pc = Ps - \Delta P1 - \Delta P2 \text{ and also}$$

$$Pc = Pr + \Delta P4 + \Delta P3.$$

where:
Pc is the bladder pressure estimate
Ps is the supply pressure from sensor 114
Pr is the return pressure from sensor 116
$\Delta P1$, $\Delta P2$, $\Delta P3$, $\Delta P4$ are the pressure drops as shown in FIG. 2.

Assuming ΔP1=ΔP4 and ΔP2=ΔP3 from the steady state flow condition as previously described, then:

$$Pc = \frac{Ps + Pr}{2} \quad \text{(Equation 1)}$$

The controller 130 may operate according to the equations:

$$Em = \left[K1\left(Pset - \frac{Ps+Pr}{2}\right) + K2\int\left(Pset - \frac{Ps+Pr}{2}\right)\right] \quad \text{(Equation 2)}$$

where
Em=voltage applied to a DC motor 120;
Pset=setpoint pressure;
K1 is a gain constant for a first term which is proportional to the error term;
K2 is a gain constant for a second term which integrates the error term to greatly reduce static offsets.

A controller which operates according to Equation 2 may also be referred to as a PI (proportional/integral) feedback control system. The generalized form is a PID (proportional/integral/differential) controller, although the inventors have found little benefit from the addition of a derivative error term in favor of the proportional error term and integral error term components of the error for use in generation of a correction voltage applied to the pump motor.

Figure 3:
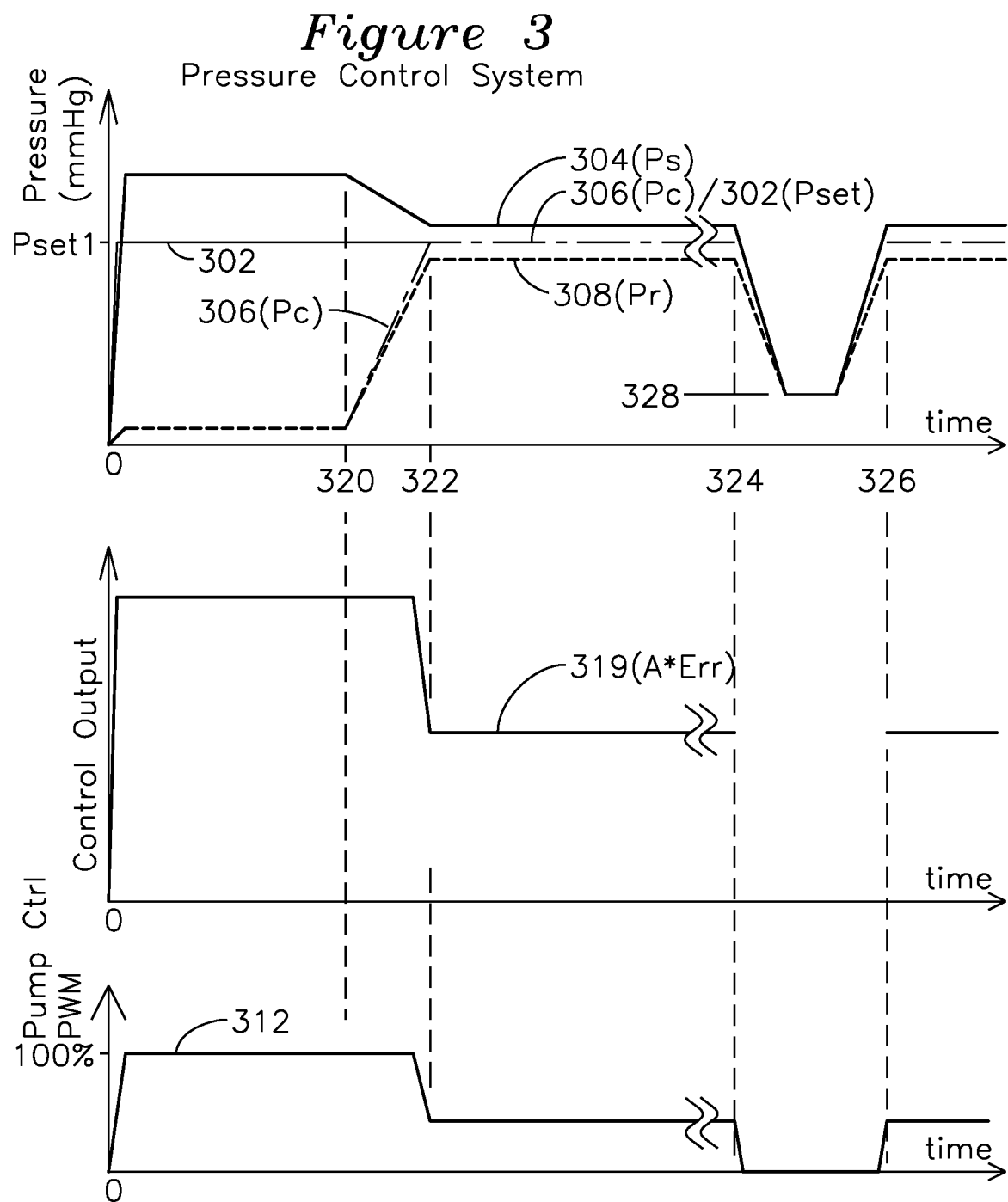
FIG. 3 shows pressure plots for operation of the system of FIG. 1.

FIG. 3 shows time-domain plots for the operation of the system starting from a rest state with a deflated bladder 109 (associated with plot Pc 306) and the pump 120 (associated with plot 312) off. Setpoint 302 Pset starts at setpoint 0 and time 0, as does supply pressure Ps 304, return pressure 308, and with pump pulse width modulation (PWM) at 0 since the error signal 310 is also at 0 since the setpoint is 0 at starting point 320. The pressure setpoint 302 ramps to Pset1, which causes a large error signal 319 through time 320 and ramps to a desired setpoint pressure 302, which is converted into pump PWM 312 going quickly from 0 at time 0 to 100% duty cycle through time 320. The pressure sensor supply pressure Ps generally follows the pump output, as shown by comparing PWM curve 312 to Ps 304. As the bladder inflates, bladder outlet flow initiates and return flows increase in the return hoses (113 and 112 of FIG. 1), causing the return flow pressure Pr 308 to ramp up until a steady state flow condition is reached at time 324, where the midpoint between Ps 304 and Pc 308 represents an accurate estimate of bladder pressure Pc 306 where the height difference L2 is negligible. In the case where L2 is a significant source of pressure offset (referred to as head pressure), this pressure may be added to the setpoint pressure, effectively placing the pressure sensors 114 and 116 at the same elevation as the cuff bladder 105. The technique of adding bladder elevation to the setpoint pressure to compensate for elevation differences between the cuff and the pressure sensors is useful where the bladder elevation is known and well controlled.

Figure 5:
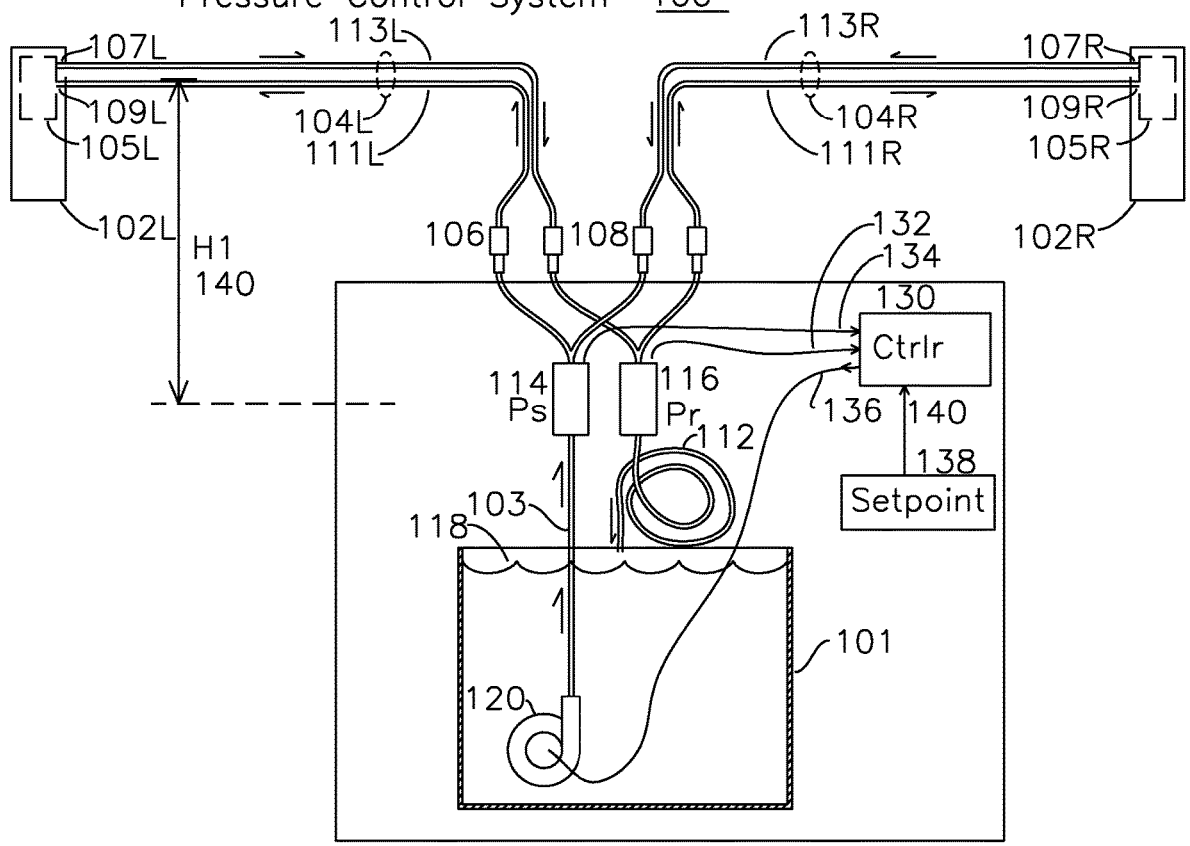
FIG. 5 shows a system diagram for a two-cuff example of the system of FIG. 1.

FIG. 5 shows the system of FIG. 1 adapted for a two cuff system having left cuff 107L and right cuff 107R, with equal length second hoses 111L and 111R and equal length third hoses 113L and 113R. The other associated elements of the two cuff system of FIG. 1 shown in FIG. 5 have L and R suffixes, with the supply pressure sensor 114 output splitting off into the two supply lines 111L and 111R, and the return pressure sensor 116 operative on the combined return lines 111L and 111R. The system of FIG. 5 is suitable for application of a pair of cuffs to the arms or legs of a human subject for application of pressurized cooling, with the arms and legs receiving a different head pressure compensation. Such a pressurized cooling system is described in U.S. Pat. No. 8,273,114. A second set of pumps and controllers may also be used with reservoir 101 to similarly provide pressurized cooling for the legs of a user, with the controller 130 operative for an arm pressure setpoint, with associated head pressure offset, which is distinct from a leg pressure setpoint and associated head pressure offset.

Another important and unexpected feature of the system of FIG. 5 is the characteristic that the pressure regulation system continues to operate accurately when the lengths of 113L/111L and 113R/111R cuff lines are different lengths. The cuff pressures developed in bladder 105L and 105R will be equal even though the lines 113L/111L are shorter or longer than lines 113R/111R. This feature provides increased flexibility in the design of cuffs and associated lines, as well as the manufacturing and deployment of the cuffs and connecting hoses. As equation 3 indicates, the requirement for equal length left hoses pair 104L and right hose pair 104R is not critical—regardless of the length of these hoses, the cuff pressure at each remote cuff will be the average pressure of Ps and Pr (ignoring head pressure H1, which may be compensated as a pressure offset as described previously). The other referenced elements of FIG. 5 operate as was described for the reference numerals of FIG. 1. In a typical configuration, the datum reference for H1 is at the elevation of pressure sensors 114 and 116, which are at the same height. In an alternative embodiment, pressure sensors 114 and 116 are at different elevations, and in this case, the datum point is the midpoint elevation of pressure sensors 114 and 116.

Figure 6:
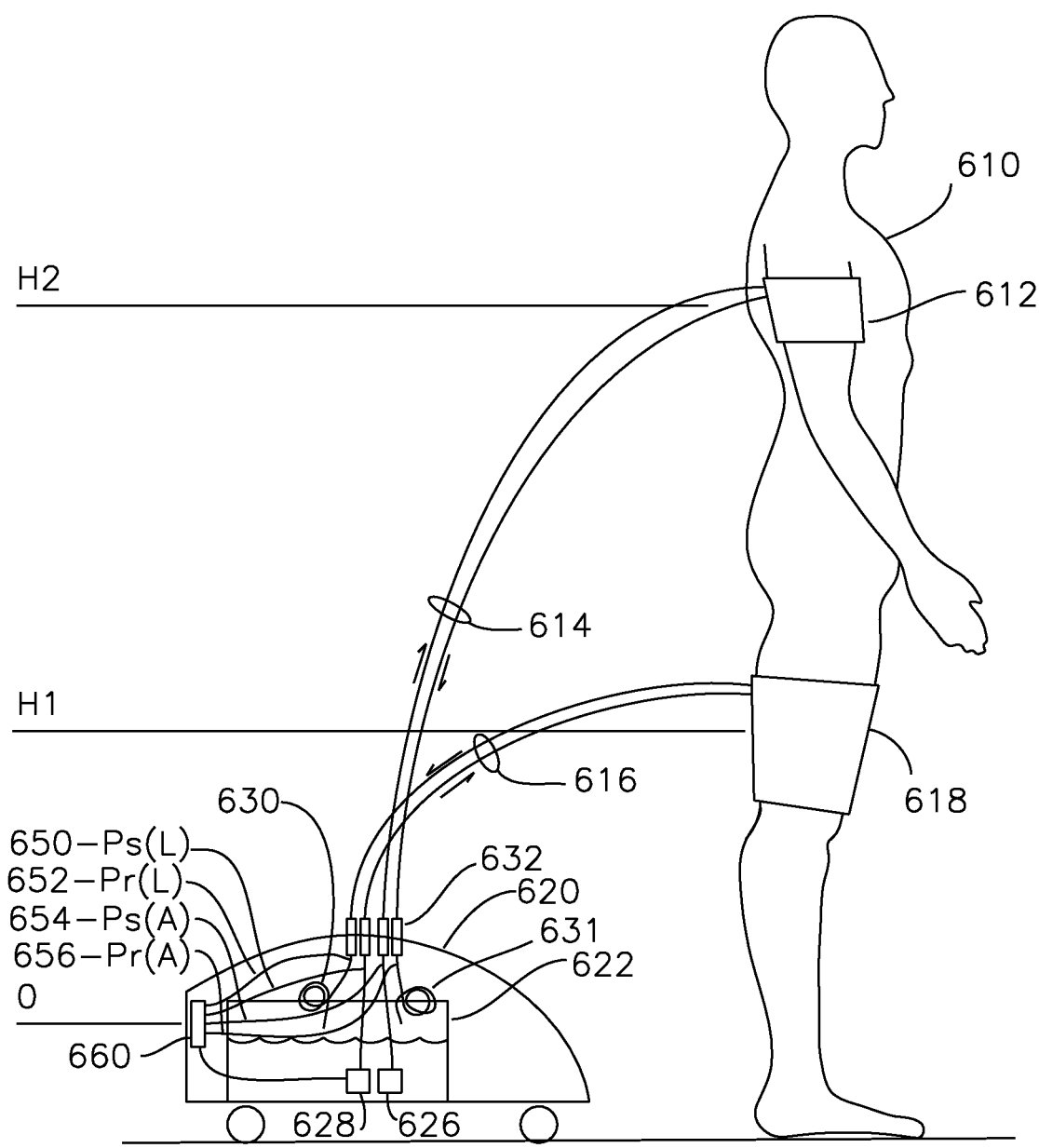
FIG. 6 shows an example pressure cooling system having two pressure regulated arm cuffs and two pressure regulated leg cuffs with cuff height head pressure compensation.

FIG. 6 shows a system 600 for arm and leg cooling and compression according to the present invention. An exercising subject 610 (exercise machine not shown) has a pair of arm cuffs 612 (one of two which may be used shown for clarity) and a pair of leg cuffs 618 (one of two which may be used shown for clarity), with the arm cuff pair connected via fluid hoses 614 to quick release couplings 632, and the leg cuff pair connected via fluid hoses 616 to quick release fittings 632. The quick release fittings 632 enable convenient separation of the cuff lines 614 and 616 from the pressure regulation coolant/pressure delivery system 620. As was described previously, the arm pressure regulation system operates independently from the leg pressure system, with the arm cuffs having a head pressure compensation distance H2 above the pressure sensor assembly 660, and the leg cuffs having a head pressure compensation distance H1 above the pressure sensor assembly 660, which may enclose the arm supply pressure sensor coupled to line 654, the arm return pressure sensor coupled to line 656, the leg supply pressure sensor 650, and the leg return pressure sensor coupled to line 652. Accordingly, arm pump 626 generates a supply pressure for arm cuff 612 which setpoint includes the head pressure offset H2, and leg pump 628 generates a supply pressure for leg cuff 618 which setpoint includes a head pressure H1 above pressure sensors 660. The pressure regulation system operates on the error term derived from the difference between setpoint and average supply and return pressure is used to form a motor control signal in the form of a pulse width modulation (PWM) of a DC voltage which varies from 0% duty cycle to 100% duty cycle. This signal has the effect of efficiently providing control of motor speed, and may be applied to motors 626 and 628 by their respective control and estimation systems, as was previously described. The distances H1 and H2 are with respect to the 0 datum of the pressure sensors 660, and are unrelated to the fill level of the reservoir 622. Arm return line 631 is shown as coiled, as is leg return line 630, which provides back pressure and flow resistance for the arm return pressure and leg return pressure sensors, respectively. Return lines 631 and 630 may be selected for inner diameter or length to provide a pressure drop in the range of 10% to 30% of the maximum pressure provided by the respective arm pump 626 and leg pump 628 at an operation flow rate which may be in the range of 2 to 20 gallons per hour (GPH), nominally 4 GPH, or where the source pressure varies from 2 pounds per square inch (psi) (nominally 100 mmHg) to 6 psi (nominally 300 mmHg) at 0 GPH flow rates, the maximum pump head pressure operating point. Higher pump pressures or flow rates may also be used. The development of back pressure may be helpful for increased delivery of pump pressure to the cuff for pressurization of the cuff, as well as the placement of the pump motor operating characteristic in an optimal pump control range for desired pressures to be developed in the cuffs. In one example of the invention, the return hose 112 of FIG. 1 is selected to provide back pressure at the return sensor 116 in the range of 25% to 50% of the pressure developed at the source pressure sensor 114, although it may vary from 10% to 80% of the source pressure. For good dynamic range control, it is typically desired in a PWM control system to operate in the range of 25% to 50% duty cycle, such that, in an example of operation of the system of FIG. 1 and with 4 GPM of flow through a single cuff 102 bladder 105, a pump 120 may operate in the range of 150 mmHg (20 kPa or 2.9 psi) pressure delivered to a supply sensor 114, experience a pressure drop of 37.5 mmHg (5 kPa, or 0.725 psi) along each flow path 111 and 113, and provide a pressure drop of 75 mmHg (10 kPa or 1.45 psi) across the return hose 112, thereby providing a measured return pressure 116 of 112.5 mmHg (15 kPa or 2.17 psi), less the head pressure drop associated with elevation H1. For H1=24" (609 mm), the resultant pressure reduction from the elevation of the cuff above the sensors would be 44 mmHg (5866 Pa, or 0.85 psi), and the pressure at the bladder 105 would be 112.5 mmHg less 44 mmHg, or 68.5 mmHg (9.132 kPa or 1.32 psi) delivered to the arm (or leg) enclosed by arm (or leg) cuff 102.

A method of determining the offset head pressure H1 of FIG. 2 directly from the in-use setup which accommodates a wide range of H1 bladder height is available in the examples of FIGS. 1 and 2 using a dynamic method shown in the time interval from 324 to 326 of FIG. 3. The pump motor may be run until a return pressure is sensed at time 322, or until equilibrium is reached at time 324. The pump is next turned off at point 324 until the measured supply pressure and measured return pressure provide only head pressure 328. This may be done after the pump shutdown and source pressure drop, with the duration from 324 to 326 governed by the dynamic behavior of Ps 304 and Pr 308, which will initially converge on a common pressure estimate and hold this pressure during the interval of time the bladders are draining. Subsequently, this head pressure estimate 328 may be used to modify the setpoint pressure to provide a compensated setpoint pressure for bladder 109 which accommodates the particular height H1, such that the average pressure of supply pressure sensor 114 and return pressure sensor 116 is now set to the setpoint pressure plus the head pressure developed by H1 and the bladder 107 pressure is now regulated to the setpoint pressure which includes elevation offsets of the cuff. The pump may be restarted and pressure regulation resumed immediately after the head pressure estimate is made, as shown in FIG. 3 at time 326.

The examples of the system are for understanding the invention only, and do not limit the invention to the particular examples shown. For example, the pumps may be direct current (DC) pumps which are controlled by a variable DC voltage, or the pumps may be DC pumps which are provided with a fixed DC voltage which is switched on and off with a duty cycle, thereby providing a pulse width modulated (PWM) equivalent voltage of the present example. Where the PWM duty cycle varies from 0 to 1, the output voltage switching between 0V and Vsupply volts, the effective DC pump motor voltage (Veffective) will be Veffective=Vsupply*PWM. Rather than changing pulse width with a fixed pulse repetition rate to accomplish PWM, it is also possible to change the pulse repetition rate for a fixed pulse width, or any other method known in the art of motor speed control. When a PWM system is used, a low loss element such as a field effect transistor (FET) may be used to minimize switching losses and resistive losses. Alternatively, the pumps may be an AC pump with a variable frequency drive, or any other drive type which provides variable speed operation. The pump may be run at constant speed and throttled using a valve, all of which are understood to be a variable speed pump motor controlled by a pump control voltage as understood in the present specification.

The term "substantially" is understood in the present specification to mean within the limits of +/−20% of the referenced pressure, length, diameter, height, or voltage, or alternatively, +/−10%.

The controller described in the present examples is a PID controller, which generates proportional and integral terms from the difference between setpoint and average of the supply and return pressure sensors. It is understood that many different types of feedback controllers are possible which operate on the setpoint and pressure sensor error voltage, including root-locus feedback controllers stabilized by use of response zeros to compensate for high frequency and low frequency poles in the response, or sigma delta controllers which perform a threshold detection on the error term. It is understood that all of these controller types known in the prior art may be used interchangably for the controller described herein.

We claim:

1. A method for regulating pressure in a pressurized cooling system comprising:
 a controller;
 a reservoir coupled to a pump, the pump providing a pressure;
 the pump coupled to, in sequence, a first hose having a first length, a supply pressure sensor coupled to a second hose having a second length, the second hose coupled to an inlet of a bladder, the bladder having an outlet coupled to a third hose having a third length, the third hose coupled to a return pressure sensor configured to return fluid pumped through the third hose to the reservoir;
 the bladder located at a first elevation different from a second elevation of at least one of the supply pressure sensor or the return pressure sensor;
 the second length being substantially equal to the third length;
 the method comprising:

estimating a pressure in the bladder by averaging a pressure sensor measurement of the supply pressure sensor and a pressure sensor measurement from the return pressure sensor;

comparing the estimated bladder pressure to a setpoint pressure to output a pump control voltage coupled to the pump;

the controller establishing the setpoint pressure by adding a head pressure offset to the desired cuff pressure, the head pressure offset derived from a difference between the first elevation and the second elevation.

2. The method of claim 1 where an inner diameter of the second hose is substantially equal to an inner diameter of the third hose.

3. The method of claim 1 where the length of the second hose and the length of the third hose each have a pressure drop during steady state operation which is greater than 10% of an outlet pressure of the pump.

4. The method of claim 1 where the first length is less than the second length or the third length.

5. The method of claim 1 where the pump is coupled to a Direct Current (DC) motor.

6. The method of claim 5 where the DC motor is actuated by a pulse width modulated (PWM) drive signal.

7. The method of claim 1 where the bladder is positioned inside a cuff which is suitable for encircling a limb.

8. The method of claim 1 where the supply pressure sensor and the return pressure sensor are at a same elevation with respect to the reservoir.

9. A method for regulating a pressurized cooling system to a desired bladder pressure, the pressurized cooling system comprising:

a reservoir operative to contain a fluid and coupled to a pump, the pump providing a pressure;

the pump coupled to, in sequence, at least one first hose having a first length, a supply pressure sensor coupled to at least one second hose having a second length, the at least one second hose coupled to at least one bladder having an inlet, the at least one bladder having an outlet coupled to at least one third hose having a third length, the at least one third hose coupled to a return pressure sensor and thereafter a fourth hose configured to return fluid pumped through the pump to the reservoir;

the second length being substantially equal to the third length;

the method operative on a controller, the method comprising:

computing an average pressure by forming a sum of a supply pressure measurement from the supply pressure sensor and a return pressure measurement from the return pressure sensor and dividing the sum by two;

computing a setpoint pressure from the desired bladder pressure plus a head pressure offset computed from an elevation difference between the bladder and at least one of the supply pressure sensor or the return pressure sensor;

outputting a pump control voltage coupled to the pump, the pump control voltage derived from a difference between the setpoint pressure and the average pressure.

10. The method of claim 9 where the at least one second hose and the at least one third hose have a substantially equal inner diameter.

11. The method of claim 9 where the at least one second hose and the at least one third hose each have a steady state pressure drop over an entire length which is greater than 10% of a supply pressure of the pump.

12. The method of claim 9 where the fourth hose provides a pressure drop over an entire length of the fourth hose which is greater than 10% of a supply pressure of the pump.

13. The method of claim 9 where the pump is a direct current (DC) pump and the pump control voltage is a pulse width modulated DC voltage.

14. The method of claim 9 where the bladder is positioned on an inner surface of a cuff operative to encircle a limb.

15. The method of claim 9 where the at least one second hose, the at least one third hose, and the at least one bladder comprise a parallel arrangement of a left and right second hose, a left and right third hose, and a left and right bladder, the parallel arrangement coupled to the supply pressure sensor and the return pressure sensor.

16. The method of claim 9 where the supply pressure sensor and the return pressure sensor are at a same elevation.

17. The method of claim 9 where the supply pressure sensor and the return pressure sensor are at different elevations.

18. The method of claim 9 where the fluid contains water, and the head pressure is substantially 9.8 Pascal per millimeter of elevation difference between the bladder and at least one of the supply pressure sensor or the return supply sensor.

19. A method for a pressure controller controlling a pressure in a system comprising:

a reservoir operative to contain a fluid and coupled to a pump;

the pump coupled to, in sequence, a first hose having a first length, a supply pressure sensor coupled to a second hose having a second length, the second hose coupled to a fluidic cuff having an inlet, the fluidic cuff having an outlet coupled to a third hose having a third length, the third hose coupled to a return pressure sensor and thereafter to a fourth hose configured to return a fluid to the reservoir;

the second length being substantially equal to the third length;

the fluidic cuff elevated above an average height of the supply pressure sensor and the return pressure sensor by a cuff height;

the method comprising:

the pressure controller receiving a setpoint pressure comprising the addition of a desired cuff pressure and a head pressure, the pressure controller having a regulation mode during which the pressure controller is configured to estimate a sensor pressure by averaging a pressure measurement from the supply pressure sensor and a pressure measurement from the return pressure sensor;

the pressure controller comparing the sensor pressure to the setpoint pressure, the pressure controller configured to output a control voltage coupled to the pump, the control voltage derived from a difference between the setpoint pressure and the sensor pressure estimate;

the pressure controller also having a head pressure measurement mode where the pump is enabled for an interval of time until the supply pressure sensor and the return pressure sensor have reached a measurement equilibrium, the pressure controller thereafter removing power to the pump and thereafter configured to determine a new head pressure by averaging a supply pressure sensor measurement and a return pressure sensor measurement, the pressure controller configured to modify the setpoint pressure by adding the new head pressure to a the desired cuff pressure.

* * * * *